United States Patent [19]
Shen et al.

[11] Patent Number: 5,268,513
[45] Date of Patent: Dec. 7, 1993

[54] AIR HYDROXYLATION OF DIAMONDOIDS

[75] Inventors: Dong-ming Shen, Langhorne, Pa.; Margaret M. S. Wu, Skillman, N.J.

[73] Assignee: Mobil Oil Corporation, Fairfax, Va.

[21] Appl. No.: 942,916

[22] Filed: Sep. 10, 1992

[51] Int. Cl.$^5$ .............................................. C07C 35/22
[52] U.S. Cl. .................................... 568/818; 568/817
[58] Field of Search .............................. 568/818, 817

[56] References Cited

U.S. PATENT DOCUMENTS

| | | | |
|---|---|---|---|
| 3,356,740 | 12/1967 | Schneider et al. | 568/818 |
| 3,356,741 | 12/1967 | Schneider et al. | 568/818 |
| 3,646,224 | 2/1972 | Moore | 260/617 |
| 4,952,747 | 8/1990 | Alexander et al. | 585/803 |
| 4,952,748 | 8/1990 | Alexander et al. | 585/803 |
| 4,952,749 | 8/1990 | Alexander et al. | 585/803 |
| 4,982,049 | 1/1991 | Alexander et al. | 585/803 |
| 5,019,665 | 5/1991 | Partridge et al. | 585/803 |
| 5,120,899 | 6/1992 | Chen et al. | 585/803 |

OTHER PUBLICATIONS

Cohen, Z. et al., *Organic Synthesis* 59, 176–182 (1980).
Cohen, Z. et al., *J. Org. Chem.* 40, 2141 (1975).
Landa, S. et al., *Z. Chem.* 7(6), 233 (1967).
Linz, T. et al., *Tetra Lett.* 28(52) 6581-2 (1987).
Moiseev, I. K. et al., *Zh. Org. Khim* 11(1), 214-15 (1975).
Burkhard, J. et al., *Gzech Patent* 161,526 (1975), see Chem. Abst 85:P123441g.
Vodicka, L. et al., *Collect. Czech. Chem. Commun.* 43(5), 1410-12 (1978).
Burkhard, J. et al., *Sb. Vys. Sk. Chem.-Technol. Praze, Technol. Paliv.* D39, 57-75 (1978), see Chemical Abstract 93:149878.
Baklan, V. F. et al., USSR SU 1,221,866 (1990), see Chemical Abstract 113:230846m.
Ashkinazi, L. A. et al., USSR SU 1,518,334 (1989), Chemical Abst. 112:P178154x.
Kovalev, V. V. et al., USSR 727,612 (1980) Chemical Abstract 93:149893w.
Shokova, E. A. et al., *Neftekhimiya* 21(2), 271-3 (1981) Chemical Abst. 95:80268t.
Granovskii, Yu V. et al., *Vestn. Mosk, Univ., Ser. 2:Khim* 27(1), 66-9 (1986) Chemical Abstract 105:190522d.
Arakawa, M. et al., JP 01,283,236 (1989); Chemical Abstract 112:197694q.
Takaishi, N. et al., *Synthesis* (4), 293–4 (1983).
Fossey, J. et al., *Can. J. Chem.* 63(3), 678–80 (1985).
Schneider, H. J. et al., *J. Org. Chem.* 50(23), 4609-15 (1985).
Murray, R. W. et al., *J. Amer. Chem. Soc.* 108(9), 2470-2 (1986).
Mello, R. et al., *J. Amer. Chem. Soc.* 111(17), 6749-57 (1989).
DePoorter, B. et al., *J. Mol. Catal.* 31(2), 221-4 (1985).
Battioni, P. et al., *J. Chem. Soc. Chem. Commun.,* 341-343 (1986).
Jones, S. R. et al., *J.C.S. Perkin I,* 2576-81 (1976).

*Primary Examiner*—Werren B. Lone
*Attorney, Agent, or Firm*—Alexander J. McKillop; Dennis P. Santini; Robert B. Furr, Jr.

[57] ABSTRACT

The invention provides a method for selectively hydroxylating a diamondoid compound to an alcohol of the diamondoid compound comprising contacting the diamondoid compound with an oxygen-containing gas under hydroxylation conditions including temperature of at least about 70° C.

16 Claims, No Drawings

AIR HYDROXYLATION OF DIAMONDOIDS

FIELD OF THE INVENTION

This invention relates to the hydroxylation of diamondoids. More specifically, this invention provides a method for hydroxylating diamondoids using air or other oxygen-containing gas as the oxidant.

BACKGROUND OF THE INVENTION

Although a large number of methods are known for the direct hydroxylation of diamondoids, none is both practical and economically feasible for large scale manufacturing. For example, the hydroxylation of adamantane can be carried out with ozone/silica gel at very low temperature (Cohen, Z. et al, *Organic Synthesis* 59, 176-182 (1980), Cohen, Z. et al., *J. Org. Chem.* 40, 2141 (1975), chromium trioxide (Landa, S. et al., *Z. Chem.* 7(6), 233 (1967), (Linz, T. et al., *Tetra. Lett.* 28(52), 6581-2 (1987)); 90-95% nitric acid (Moiseev, I.K. et al., *Zh. Org. Khim* 11(1), 214-15 (1975)); 65% nitric acid with $Br_2$ or KBr or HBr (Burkhard, J. et al., *Czech Patent* 161,526 (1975), see Chemical Abstract 85:P123441g); Vodicka, L. et al., *Collect. Czech. Chem. Commun.* 43(5), 1410-12 (1978), Burkhard, J. et al., *Sb. Vvs. Sk. Chem.-Technol. Praze, Technol. Paliv.* D39, 57-75 (1978), see Chemical Abstract, 93:149878)); fuming sulfuric acid (U.S. Pat. No. 3,646,224 to Moore); $Br_2$—$H_2O$ (Kaklan, V. F. et al., USSR SU 1,221,866 (1990)): $K_2Cr_2O_7$-$Bu_4NI$-benzene (Ashkinazi, L. A. et al., USSR SU 1,518,334 (1989), Chemical Abstract 112:P178154x)); t-BuOH-$CF_3CO_2H$ (Kovalev, V.V. et al., USSR 727,612 (1980), Shokova, E.A. et al., *Neftekhimiva* 21(2), 271-3 (1981), Granovskii, Yu V. et al., *Vestn. Mosk. Univ., Ser. 2:Khim* 27(1), 66-9 (1986)); t-BuOH and conc. $H_2SO_4$ in acetonitrile-hexane (Arakawa, M. et al., JP 01,283,236 (1989)); peracids (with MCPBA: Takaishi, N. et al., *Synthesis* (4), 293-4 (1983)); with perbenzoic acid (Fossey, J. et al., *Can. J. Chem.* 63(3), 678-80 (1985)); substituted perbenzoic acids (Schneider, H.J. et al., *J. Org. Chem.* 50(23), 4609-15 (1985)); dioxiranes (dimethyldioxirane: Murray, R.W. et al., *J. Amer. Chem. Soc.* 108(9), 2470-2 (1986); methyltrifluoromethyldioxirane (Mello, R. et al., *J. Amer. Chem. Soc.* 111(17), 6749-57 (1989)); NaOCl or NaOBr or $H_2O_2$ with manganese porphyrin (with NaOX: DePoorter, B. et al., *J Mol. Catal.* 31(2), 221-4 (1985); $H_2O_2$ De Poorter, B. et al., *J. Chem. Soc. Chem. Commun.* (4), 341-3 (1986)); t-BuOOH with heteropolytungstate (Faraj, M. et al., *J. Chem. Soc. Chem. Commun.* (19), 1487-9 (1987)); concentrated sulfuric acid in $(CF_3CO)_2$ (Kovalev, V. V. et al., *Zh. Oro. Khim.* 23(9), 1882-6 (1987)); $F_2$ in water-acetonitrile (Rozen, S. et al., *J. Amer. Chem. Soc.* 111(21), 8325-6 (1989)); or oxone (Kumaranthasan, R. et al., *Org. Prep. Proceed. Int.*, 23(5), 651-4 (1991)

The foregoing syntheses are hindered by one or more of the following: low selectivity, high cost, large amounts of hazardous wastes requiring disposal, large amounts of expensive solvents, dangerous reagents, and very corrosive chemicals. While it would be desirable to provide a commercially useful and less expensive alternative previous studies have not provided a method for the direct hydroxylation of adamantane (Smith, G. W. et al., *J. Org. Chem.* 26, 2207-12 (1961): Landa, S. et al., *Sb. Vvs. Sk. Chem.-Technol. Praze, Technol. Paliv.* 19, 5-17 (1969), see Chemical Abstract, 74:99507h). While the Landa article addressed oxygen addition to adamantane, the disclosed method evolved adamantanone (the mono-ketone) rather than the alcohol produced by the method of this invention. Both studies used acetic acid as solvent or co-solvent and resulted in low selectivity for 1-adamantanol.

SUMMARY OF THE INVENTION

This invention provides a method for the direct hydroxylation of diamondoids using an oxygen-containing gas such as air as the oxidant. In one embodiment, the method of the invention selectively converts adamantane (in an alkane solvent such as n-hexane) to 1-adamantanol and 1,3-dihydroxyadamantane in the presence of air at elevated temperature. In another embodiment, the invention provides a method for selectively hydroxylating a diamondoid compound to the bridgehead monoalcohol or poly-alcohols of a diamondoid compound comprising contacting the diamondoid compound with air in the absence of added catalyst under hydroxylation conditions including temperature of from about 70 to about 200° C. The diamondoid reactants may be neat or may be reacted in the presence of a suitable solvent, and no halogenated diamondoid feedstock is required. As used herein, the term "diamonoid" is used in its usual sense, to designate a family of polycyclic alkanes including adamantane, diamantane, and triamantane, as well as the higher analogs and their substituted derivatives, examples of which include ethyl- and methyl-substituted diamondoids. The term "diamond" can be a pure component or a mix. For a survey of the chemistry of diamondoid molecules, see Fort, Raymond C., *Adamantane, The Chemistry of Diamond Molecules* (1976) as well as U.S. Pat. 5,019,660 to Chapman and Whitehurst and 5,053,434 to Chapman. Diamondoid feedstocks useful in the present invention may be synthesized or may be recovered from natural sources, for example, from certain natural gas deposits.

U.S. Pat. Nos. 4,952,747, 4,952,748, 4,952,749 and 4,982,049 teach methods for recovering diamondoid compounds from a natural gas stream containing the same. U.S. Pat. No. 5,019,665 teaches a method for concentrating diamondoids which are dissolved in a paraffinic solvent. U.S. Pat. No. 5,120,899 teaches a method for recovering diamondoid compounds from a natural gas stream to produce a diamondoid mixture which is substantially free of solvent contamination. The entire text of the patents cited above is incorporated herein by reference for details of diamondoid compound chemistry and production.

This invention provides a practical functionalization procedure for the derivatization of diamondoids. The hydroxy derivatives of diamondoids are useful not only as chemical intermediates, but also as lubricant precursors, zeolite directing agents, bulky polar solvents for laboratory and industrial syntheses, as well as for pharmaceutical applications as antiviral agents.

The method of the invention is effective in the presence or absence of added solvent. Nonpolar solvents improve selectivity for the desired alcohol products. Examples of the preferred nonpolar solvents include paraffinic hydrocarbons having from about 4 to about 20 carbon atoms, of which butane, pentane, hexane, heptane, and octane are preferred, and n-hexane is particularly preferred. Thus while it is preferred to use a solvent in the method of the invention, it is not believed to be a critical aspect of the invention. That the method of the invention is effective with neat diamondoid reactants is unexpected because the reactant mixtures can include (as major components) high melting-point solids which readily sublime.

The method is effective with or without free-radical initiators. Metal additives, for example, metal salts such as such as Mn or Ni acetate, improve conversion and decrease selectivity to the undesired diamondoid carbonyl compounds such as the diamondoid aldehydes. If the metal additives are used, it is preferred to dissolve the diamondoid reactants in a suitable solvent.

The method of the invention operates under a broad range of temperatures and pressures. For example, useful temperatures generally range from about ambient to about 300° C., preferably from about 70 to about 200° C., and more preferably from about 100 to about 150° C. Useful reaction pressures typically fall within the range of from subatmospheric to about 1500 psig, preferably from about 100 to about 1000 psig, and more preferably from about 250 to about 600 psi. Lower pressures of around 1 atmosphere, favor conversion of adamantane to 2-adamantanol and adamantanone; while adamantane conversion at higher pressures (e.g., from about 300 to about 1000 psi) yields product enriched in 1-adamantanol.

EXAMPLES

Examples 1 through 16 show the hydroxylation of adamantane in accordance with the present invention. Except for Example 1, which was carried out in glassware at 1 atm, all Examples were obtained using a 600-mL SS Parr reactor. A typical run used 13.62 g of adamantane in 50 mL of solvent. The reactor was pressurized with air and heated carefully to the desired temperature with minimum overheating. When about ½ to ⅔ of the oxygen in the reactor was consumed, pure oxygen was introduced to the reactor to make up the loss. At the end of the reaction, the reactor was cooled, vented, and opened. Enough acetone (usually 50 mL) was added to the mixture and organic solid in the product dissolved to give a homogeneous solution before it was analyzed with GC to give the composition of the products. Methylene chloride (25-50 mL) was optionally added as required to facilitate the dissolution of the product.

Examples 1-7: Temperature and Pressure Effects

Examples 1 through 7 investigated the effect of temperature and pressure on the hydroxylation of adamantane. The highest selectivity for bridgehead hydroxylation was obtained at 130° C. and 420 psi.

Examples 4, 8, and 9: Solvent Effects

Examples 4, 8, and 9 investigated the effect of solvents on the hydroxylation of adamantane at 130° C. and about 420 psi (initial pressure of 300° C. at room temperature). The polar solvents gave low selectivity for the bridgehead alcohol and high selectivity to the undesirable adamantanone. The selectivity ratio of adamantanone to 2-adamantanol of Example 9 in Table 2 was 43, much higher than that of Example 4 (2.9). The polar solvent also gave low adamantane conversion, 24% vs. 57% conversion in hexane solvent. N-hexane is a particularly preferred solvent for air oxidation of adamantane to alcohols in accordance with the invention.

Examples 4, 10, and 11: Free Radical Initiators

Examples 4, 10, and 11 investigated the effect of initiators on the hydroxylation of adamantane. These runs were carried out using n-hexane as the solvent at 130° C. and about 420 psi (initial pressure of 300 psi at room temperature). The results of two peroxide initiators and a blank run were shown in Table 3. The results of the three runs were very similar. The slight variations in selectivity ratios were attributable to the variation in the extent of conversion. These results showed that the hydroxylation proceeded with good conversions and selectivities with or without radical initiators.

Examples 4 and 12-16: Metal Salts

Examples 4 and 12-16 investigated the effect of adding metal salts on the hydroxylation of adamantane at 130° C. and about 420 psi (initial pressure of 300 psi at room temperature) in n-hexane. Metal acetate (0.75% by molar to adamantane) was added, and the results were shown in Table 4. Adding manganese or nickel salts increased conversions from 57% (Ex. 4) to 65% (Ex. 12) or 62% (Ex. 14). Selectivities to the undesirable adamantanone decreased slightly by adding Mn or Ni acetate.

Examples 17 and 18: Mixed Diamondoid Feed

Examples 17 and 18 were directed to air hydroxylation of mixed diamondoids. For these two runs, the products were separated by filtration on silica gel with three different solvents to collect unreacted diamondoid hydrocarbon, mono-alcohols, and dialcohols fractions. The solvents used were hexanes, 1:9 (v/v) acetone:hexanes mixture, and acetone, respectively. This gives a relatively clean separation of the three types of products. The results are summarized in Table 5. Example 17 used n-hexane as solvent; while Example 18 used neat diamondoids. No sublimation of solid to the top of the reactor was observed in either case.

Changes and modifications in the specifically described embodiments can be carried out without departing from the scope of the invention which is intended to be limited only by the scope of the appended claims.

TABLE 1

EFFECT OF TEMPERATURE AND PRESSURE ON ADAMANTANE OXIDATION **

| Example Number | T. °C. | P, psi | Time Hrs. | % Ad—H Convers. | % Selectivity for 1-AdOH | % Selectivity for 1,3-Ad(OH)$_2$ | $\dfrac{3°C-H^*}{2°C-H}$ | $\dfrac{1\text{-AdOH}}{1,3\text{-Ad(OH)}_2}$ | $\dfrac{Ad=O}{2\text{-AdOH}}$ |
|---|---|---|---|---|---|---|---|---|---|
| 1 | 130 | 14.7 | ~17 | 5.9 | 63.8 | 0.0 | 2.8 | ∞ | 0.48 |
| 2 | 130 | 120 | ~15 | 29.0 | 85.2 | 1.3 | 8.9 | 18.5 | 0.26 |
| 3 | 130 | 575 | ~20 | 55.1 | 62.5 | 14.4 | 9.0 | 4.3 | 3.2 |
| 4 | 130 | 420 | ~25 | 57.1 | 63.8 | 16.9 | 11.5 | 3.8 | 2.9 |
| 5 | 130 | 300 | 10.5 | 56.5 | 61.4 | 15.9 | 8.9 | 3.9 | 2.4 |
| 6 | 120 | 420 | ~15 | 42.6 | 73.2 | 9.8 | 8.3 | 7.5 | 1.3 |

TABLE 1-continued
EFFECT OF TEMPERATURE AND PRESSURE ON ADAMANTANE OXIDATION**

| Example Number | T, °C. | P, psi | Time Hrs. | % Ad—H Convers. | % Selectivity for 1-AdOH | % Selectivity for 1,3-Ad(OH)$_2$ | Selectivity Ratios $\frac{3°C-H*}{2°C-H}$ | $\frac{1\text{-AdOH}}{1,3\text{-Ad(OH)}_2}$ | $\frac{\text{Ad}=O}{2\text{-AdOH}}$ |
|---|---|---|---|---|---|---|---|---|---|
| 7 | 120 | 290 | 11 | 29.6 | 73.4 | 6.6 | 8.2 | 11.2 | 0.8 |

These two runs No 1 and 2, used n-octane as solvent, all others used n-hexane.

\* $\frac{3°C-H}{2°C-H} = \frac{\% \text{ 1-AdOH} + \% \text{ 1,3-Ad(OH)}_2}{\% \text{ Ad}=O + \% \text{ 2-AdOH}}$ \*\* Ad = adamantyl group

TABLE 2
EFFECT OF SOLVENTS ON ADAMANTANE OXIDATION

| Example Number | Solvent | Time Hrs. | % Ad—H Convers. | % Selectivity for 1-AdOH | % Selectivity for 1,3-Ad(OH)$_2$ | $\frac{3°C-H}{2°C-H}$ | $\frac{1\text{-AdOH}}{1,3\text{-Ad(OH)}_2}$ | $\frac{\text{Ad}=O}{2\text{-AdOH}}$ |
|---|---|---|---|---|---|---|---|---|
| 4 | n-hexane | ≈25 | 57.1 | 63.8 | 16.9 | 11.5 | 3.8 | 2.9 |
| 8 | acetone | 11 | 64.7 | 58.7 | 16.6 | 4.6 | 3.5 | 3.4 |
| 9 | acetic acid | 7 | 23.7 | 33.2 | 16.3 | 4.4* | 2.5* | 43 |

\* Include selectivity of 1-Ad—OAc for 7.7%.

TABLE 3
EFFECT OF INITIATORS ON ADAMANTANE OXIDATION

| Example Number | Initiator | Time Hrs. | % Ad—H Convers. | % Selectivity for 1-AdOH | % Selectivity for 1,3-Ad(OH)$_2$ | $\frac{3°C-H}{2°C-H}$ | $\frac{1\text{-AdOH}}{1,3\text{-Ad(OH)}_2}$ | $\frac{\text{Ad}=O}{2\text{-AdOH}}$ |
|---|---|---|---|---|---|---|---|---|
| 4 | t-(BuO)$_2$ | ~25 | 57.1 | 63.8 | 16.9 | 11.5 | 3.8 | 2.9 |
| 10 | t-BuOOH | ~16 | 49.0 | 69.8 | 11.6 | 11.8 | 6.1 | 1.1 |
| 11 | none | 10.5 | 58.4 | 63.4 | 16.6 | 10.4 | 3.8 | 1.8 |

TABLE 4
EFFECT OF METAL SALTS ON ADAMANTANE OXIDATION

| Example Number | Metal Salt | Time Hrs. | % Ad—H Convers. | % Selectivity for 1-AdOH | % Selectivity for 1,3-Ad(OH)$_2$ | $\frac{3°C-H}{2°C-H}$ | $\frac{1\text{-AdOH}}{1,3\text{-Ad(OH)}_2}$ | $\frac{\text{Ad}=O}{2\text{-AdOH}}$ |
|---|---|---|---|---|---|---|---|---|
| 4 | None | ~25 | 57.1 | 63.8 | 16.9 | 11.5 | 3.8 | 2.9 |
| 12 | Mn(OAc)$_2$H$_2$O | ~14 | 65.3 | 60.0 | 18.9 | 10.2 | 3.2 | 2.1 |
| 13 | Co(OAc)$_2$ | 15 | 70.2 | 53.0 | 18.7 | 5.5 | 2.8 | 4.8 |
| 14 | Ni(OAc)$_2$ | 10 | 62.0 | 62.3 | 17.9 | 11.6 | 3.5 | 1.2 |
| 15 | Fe(OAc)$_3$ | 11.5 | 46.1 | 72.5 | 10.9 | 10.0 | 6.6 | 0.7 |
| 16 | Co(acac)$_2$ | 10 | 63.3 | 55.1 | 16.2 | 4.7 | 3.4 | 4.8 |

TABLE 5
AIR HYDROXYLATION OF DIAMONDOID MIXTURE AT 130 C.

| Example Number | Pressure (Psi) | Time Hrs. | Initiator wt. % | Weight & of Products vs. Starting Material Hydrocarbon | Mono-alcohols | Di-alcohols |
|---|---|---|---|---|---|---|
| 17 | 650–1165 | 4 | 1.3 | 56.1 | 29.5 | 10.2 |
| 18 | 570–685 | 6 | 0.90 | 33.5 | 38.4 | 16.0 |

What is claimed is:

1. A method for selectively hydroxylating a diamondoid compound to an alcohol of said diamondoid compound comprising contacting said diamondoid compound with an oxygen-containing gas at temperature of from about 70° C. to about 200° C. and pressure of from 100 to 1000 psig in the absence of added catalyst.

2. The method of claim 1 wherein said pressure is from about 300 to about 1000 psig.

3. The method of claim 1 wherein said hydroxylation conditions include temperature of at least about 100° C.

4. The method of claim 1 wherein said hydroxylation conditions include temperature of from about 100 to about 150° C. and pressure of from about 250 to about 600 psig.

5. The method of claim 1 further comprising contacting said diamondoid compound with said oxygen-containing gas in the presence of a non-diamondoid alkane solvent.

6. The method of claim 5 wherein said alkane solvent comprises at least one normal alkane.

7. The method of claim 6 wherein said linear alkane is n-hexane.

8. A method for selectively hydroxylating a diamondoid compound to the bridgehead monoalcohol of said diamondoid compound comprising contacting said diamondoid compound with air in the absence of added catalyst under hydroxylation conditions including temperature of from about 70 to about 200° C. and pressure of from about 300 to about 1000 psig.

9. The process of claim 8 wherein said diamondoid compound is dissolved in a solvent comprising a majority of substituted diamondoid compounds.

10. The process of claim 8 wherein said diamondoid compound is dissolved in a solvent consisting essentially of diamondoid compounds.

11. The method of claim 1 further comprising contacting said diamondoid compound with said oxygen-containing gas in the presence of a free radical initiator.

12. The method of claim 1 further comprising contacting said diamondoid compound with said oxygen-containing gas in the presence of peroxide.

13. The method of claim 1 further comprising contacting said diamondoid compound with said oxygen-containing gas in the presence of a metal.

14. The method of claim 13 wherein said metal is present in the form of a metal salt.

15. The method of claim 14 wherein said metal salt comprises metal acetate.

16. The method of claim 14 wherein said metal salt comprises Mn or Ni.

* * * * *